US006413267B1

(12) United States Patent
Dumoulin-White et al.

(10) Patent No.: US 6,413,267 B1
(45) Date of Patent: Jul. 2, 2002

(54) THERAPEUTIC LASER DEVICE AND METHOD INCLUDING NONINVASIVE SUBSURFACE MONITORING AND CONTROLLING MEANS

(75) Inventors: Roger J. Dumoulin-White; Lothar Lilge; Robert A. Weersink, all of Ontario (CA)

(73) Assignee: Theralase, Inc., Markham (CA)

( * ) Notice: Subject to any disclaimer, the term of this patent is extended or adjusted under 35 U.S.C. 154(b) by 0 days.

(21) Appl. No.: 09/370,315

(22) Filed: Aug. 9, 1999

(51) Int. Cl.[7] ............................................... A61N 5/006
(52) U.S. Cl. ............................... 607/89; 607/88; 606/3; 606/12; 128/898
(58) Field of Search .......................... 606/2, 3, 7–12, 606/127, 128; 128/898; 607/88, 89, 94

(56) References Cited

U.S. PATENT DOCUMENTS

| | | | |
|---|---|---|---|
| 4,215,694 A | 8/1980 | Isakov et al. | |
| 4,640,283 A | 2/1987 | Sawa et al. | |
| 4,644,948 A | 2/1987 | Lang et al. | |
| 4,671,285 A | 6/1987 | Walker | |
| 4,724,835 A | 2/1988 | Liss et al. | |
| 4,733,660 A | 3/1988 | Itzkan | |
| 4,930,504 A | 6/1990 | Diamantopoulos et al. | |
| 4,930,505 A | 6/1990 | Hatje | |
| 4,963,143 A | 10/1990 | Pinnow | |
| 4,966,144 A | 10/1990 | Rochkind et al. | |
| 4,973,848 A | * 11/1990 | Kolobanov et al. | 205/458.1 |
| 5,029,581 A | 7/1991 | Kaga et al. | |
| 5,050,597 A | 9/1991 | Daikuzono | |
| 5,051,823 A | 9/1991 | Cooper et al. | |
| 5,057,009 A | * 10/1991 | Rink | 606/12 |
| 5,071,417 A | * 12/1991 | Sinofisky | 606/8 |
| 5,150,704 A | 9/1992 | Tatebayashi et al. | |
| 5,154,707 A | 10/1992 | Rink et al. | |
| 5,269,778 A | * 12/1993 | Rink et al. | 606/12 |
| 5,320,619 A | 6/1994 | Badawi | |
| 5,344,434 A | 9/1994 | Talmore | |
| 5,354,323 A | 10/1994 | Whitebook | |
| 5,358,503 A | * 10/1994 | Bertwell et al. | 606/27 |
| 5,409,482 A | 4/1995 | Diamantopoulos | |
| 5,423,801 A | 6/1995 | Marshall et al. | |

(List continued on next page.)

FOREIGN PATENT DOCUMENTS

| | | |
|---|---|---|
| EP | 0 421 030 A | 4/1991 |
| EP | 0 435 506 A | 7/1991 |
| EP | 0 815 797 A | 1/1998 |

OTHER PUBLICATIONS

Abe, Tatsuhide, "Diode Laser LLLT–Enhanced Bone Fusion of Femoral Shaft Fracture Complicated By Chronic Osteomyelitis: A Case Report," pp. 175–178, 1990.

(List continued on next page.)

Primary Examiner—John Mulcahy
Assistant Examiner—Ahmed Farah
(74) Attorney, Agent, or Firm—Caesar, Rivise, Bernstein, Cohen & Pokotilow, Ltd.

(57) ABSTRACT

A method is provided for treating a patient having a disorder, wherein the method includes irradiating a tissue surface of the patient with at least one laser beam, automatically monitoring the tissue, and automatically controlling the at least one laser beam to adjust and/or terminate the treatment in a therapeutically effective manner. The method noninvasively determines in real-time the irradiance and/or radiant exposure of a target tissue at a predetermined depth below the tissue surface by detecting the radial dependence of light remitted from the tissue surface. Preferably, the method employs a near-infrared light laser beam and a visible laser light beam in combination. An apparatus for performing the method is also provided.

23 Claims, 3 Drawing Sheets

U.S. PATENT DOCUMENTS

| | | | |
|---|---|---|---|
| 5,445,146 A | * 8/1995 | Bellinger | 607/89 |
| 5,445,608 A | 8/1995 | Chen et al. | |
| 5,464,436 A | 11/1995 | Smith | |
| 5,514,168 A | 5/1996 | Friedman | |
| 5,616,140 A | 4/1997 | Prescott | |
| 5,649,924 A | 7/1997 | Everett et al. | |
| 5,657,760 A | 8/1997 | Ying et al. | |
| 5,755,752 A | 5/1998 | Segal | |
| 6,074,382 A | * 6/2000 | Asah et al. | 606/9 |
| 6,165,170 A | * 12/2000 | Wynne et al. | 606/9 |

OTHER PUBLICATIONS

Asada et al., "Diode Laser Therapy for Rheumatoid Arthritis: A Clinical Evaluation of 102 Joints Treated with Low Reactive–Level Laser Therapy (LLLT)," pp. 147–151, 1989.

Farrell et al., "A diffusion theory model of spatially resolved, steady–state diffuse reflectance for the noninvasive determination of tissue optical peoferties in vivo," Medical Physics, vol. 19, No. 4, pp. 879–888, 1992.

McKibbin et al., "A Statistial Study on the Use of the Infrared 904 –nm Low Energy Laser on Calcaneal Spurs," Journal Medicine & Surgery, pp. 71–77, Feb. 1991.

Mester et al., "Wound–Healing," pp. 7–15, 1989.

Ohshiro et al., "Retroactive Study in 524 Patients on the Application of the 830 nm GaAlAs Diode Laser in Low Reactive–Level Laser Therapy (LLLT) for Lumbago," pp. 121–126, 1992.

Shiroto et al., "Retrospective Study of Diode Laser Therapy for Pain Attenuation in 3635 Patients: Detailed Analysis by Questionnaire," pp. 41–47, 1989.

Trelles et al., "The Action of Low Reactive Level Laser Therapy (LLlT) on Mast Cells: A possible pain relief mechanism examined," pp. 27–30, 1989.

Vasseljen, Ottar, "Low–level laser versus Traditional Physiotherpy in the Treatment of Tennis Elbow," Physiotherapy, vol. 78, No. 5, pp. 329–334, May 1992.

Weersink et al., "Accuracy of Noninvasive in vivo Measurements of Photosensitizer Uptake Based on a Diffusion Model of Reflectance Spectroscopy," Photochemistry and Photobiology, 66(3), pp. 326–335, 1997.

Zheng et al., "The Activating Action of Low Level Helium Neon Laser Radiation on Macrophages in the Mouse Model," pp. 55–58, 1992.

* cited by examiner

FIG. 3
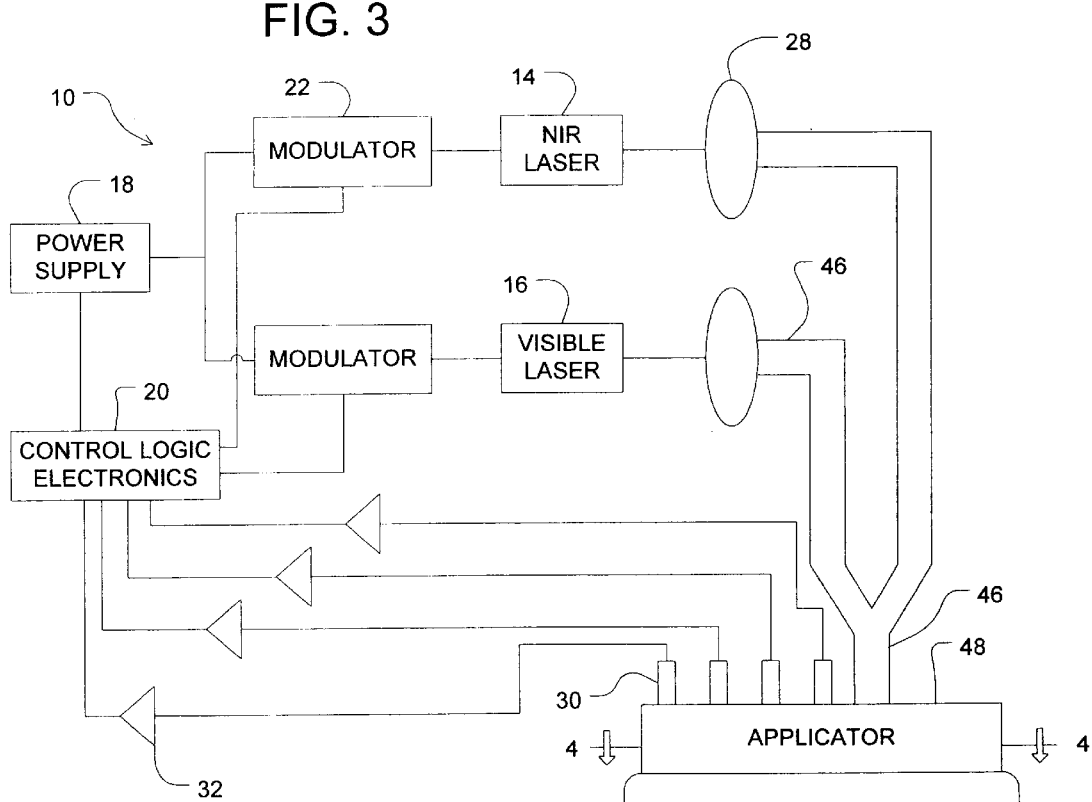
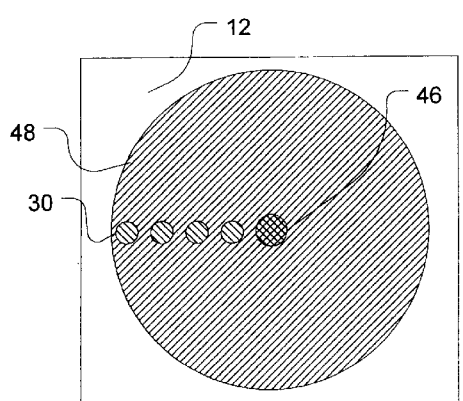
FIG. 4 ial., U.S. Pat. No. 5,755,752 to Segal.
THERAPEUTIC LASER DEVICE AND METHOD INCLUDING NONINVASIVE SUBSURFACE MONITORING AND CONTROLLING MEANS

FIELD OF THE INVENTION

This invention relates to methods and devices for treating soft tissue disorders, and more particularly to laser therapeutic methods and devices.

BACKGROUND OF THE INVENTION

Therapeutic lasers are useful in the treatment of certain types of tissue disorders. See, e.g., U.S. Pat. No. 4,215,694 to Isakov et al., U.S. Pat. No. 4,640,283 to Sawa et al., U.S. Pat. No. 4,671,285 to Walker, U.S. Pat. No. 4,724,835 to Liss et al., U.S. Pat. No. 4,930,504 to Diamantopoulos et al., U.S. Pat. No. 4,930,505 to Hatje, U.S. Pat. No. 4,966,144 to Rochkind et al., U.S. Pat. No. 5,029,581 to Kaga et al., U.S. Pat. No. 5,051,823 to Cooper et al., U.S. Pat. No. 5,150,704 to Tatebayashi et al., U.S. Pat. No. 5,320,619 to Badawi, U.S. Pat. No. 5,344,434 to Talmore, U.S. Pat. No. 5,409,482 to Diamantopoulos, U.S. Pat. No. 5,445,146 to Bellinger, U.S. Pat. No. 5,445,608 to Chen, U.S. Pat. No. 5,464,436 to Smith, U.S. Pat. No. 5,514,168 to Friedman, U.S. Pat. No. 5,616,140 to Prescott, U.S. Pat. No. 5,649,924 to Everett et al., U.S. Pat. No. 5,755,752 to Segal.

Laser therapy (i.e., Low Level Laser Therapy or LLLT) generally requires the injured tissue to be exposed directly to the laser light for predetermined intervals of time. Exposure to laser light not only lessens the pain associated with certain disorders, but actually speeds the healing of the treated tissues. The wavelength of the laser light, the intensity of the laser light and the exposure time are important factors when selecting a specific treatment protocol for a specific disorder.

The wavelength of the laser light affects its ability to penetrate through overlaying tissues, such as skin, to reach the tissues and molecules of interest. For example, red light is attenuated by most tissues ($1/e^2$ attenuation), and thus the penetration depth is less than 1 cm into such tissues, whereas near-infrared (NIR) light is less attenuated by most tissues, and thus can penetrate more than 1 cm into such tissues.

The wavelength of the laser light also affects it ability to promote biological pathways for healing injured tissues. For example, the quantum energy of near-infrared photons is small, and thus near-infrared photons have a relatively low potential to electronically exciting biomolecules. On the other hand, the quantum energy of red wavelength photons is sufficient to achieve electronic excitation of biomolecules, potentially promoting direct photochemical and photobiological effects in target tissues.

The precise nature of the molecular events caused by narrow bandwidth red and near-infrared light irradiation is still under investigation. However, clinical evidence suggests that biostimulation using red light and biostimulation using near-infrared light each promotes wound healing and/or relieves the symptoms of rheumatoid arthritis. See, e.g., Mester et al., "Wound-Healing," 1 Laser Therapy 7–15 (1989), and Asada et al., "Diode Laser Therapy for Rheumatoid Arthritis: A Clinical Evaluation of 102 Joints Treated with Low Reactive-Level Laser Therapy (LLLT) 1 Laser Therapy 147–152 (1989).

The intensity of the laser light used to treat an injury is another factor in its effectiveness. Applying a therapeutically insufficient intensity of laser light to an injury has no desirable effects, but applying excess intensity can cause undesirable heating, burning and even vaporization of tissue.

The total exposure time is also an important factor in laser therapy, as combined with irradiance it determines the total deposited energy. If an injury is not exposed to laser light for an appropriate interval of time, insufficient healing may result. Excess exposure to laser light can injure the target tissues.

As the target tissue for laser therapy is typically subcutaneous, and the factors controlling the penetrability of a patient's skin (e.g., thickness, fat content, color, etc.) vary from patient to patient, it has been difficult to employ one ideal protocol for all patients. That is, the target tissue is typically located at a certain depth "$Z_0$" below the surface, and the energy delivered to depth "$Z_0$" has been difficult to monitor and control. Protocols can be manually adjusted to the particular patient, but this adds complexity to the treatment, and more heavily relies on the proper training of medical personnel.

A variety of laser systems in the laser therapy and laser surgery arts have been proposed that intelligently control laser beam intensity and duration using target monitoring and feedback (real-time and otherwise). See, e.g., U.S. Pat. No. 5,657,760 to Ying, U.S. Pat. No. 5,423,801 to Marshall, U.S. Pat. No. 5,354,323 to Whitebook, U.S. Pat. No. 5,154,707 to Rink et al., U.S. Pat. No. 5,050,597 to Daikuzono, U.S. Pat. No. 4,973,848 to Kolobanov et al., and U.S. Pat. No. 4,644,948 to Lang et al.

All references cited herein are incorporated herein by reference in their entireties.

SUMMARY OF THE INVENTION

The invention provides a method for treating a patient having a disorder, said method comprising:
  is irradiating a tissue of said patient with a near-infrared laser light having a first therapeutically effective intensity and with a visible laser light having a second therapeutically effective intensity;
  automatically monitoring said irradiated tissue; and
  automatically terminating said irradiating when said monitoring indicates that said near-infrared laser light and said visible laser light have been applied to said tissue for a duration therapeutically effective to treat said disorder.

Also provided is a laser apparatus adapted to perform this method of the invention, said laser apparatus comprising:
  a near-infrared light laser;
  a visible light laser;
  a power supply in electrical communication with said lasers;
  waveguides for guiding beams from said lasers to a common focal point on a surface of a target tissue;
  detectors adapted to detect radiation remitted from said target surface along a radius originating at said common focal point; and
  control logic electronics adapted to automatically adjust an output of said lasers based on said remitted radiation detected by said detectors.

The invention also provides a method for administering a predetermined dose of radiation to a distal target tissue, said method comprising:
  irradiating a proximal tissue adjacent said distal target tissue with at least one laser light which penetrates through said proximal tissue to administer radiation to said distal target tissue;
  automatically monitoring said proximal tissue to determine whether to terminate said irradiating, said monitoring comprising detecting a radial dependence of a diffuse reflectance from a surface of said proximal tissue of said at least one laser light; and automatically terminating said irradiating when said monitoring indicates that said predetermined dose of laser light has been applied to said distal target tissue.

A laser apparatus adapted to perform this method of the invention is also provided. The laser apparatus comprises:

at least one laser;

a power supply in electrical communication with said at least one laser;

at least one detector adapted to detect radiation remitted from two points on said target surface along a radius originating at a focal point of said at least one laser on said proximal tissue; and control logic electronics adapted to automatically adjust an output of said at least one laser based on said remitted radiation detected by said at least one detector.

BRIEF DESCRIPTION OF THE DRAWINGS

The invention will be described in conjunction with the following drawings in which like reference numerals designate like elements and wherein:

FIG. 3 is a schematic block diagram of another embodiment of the invention; and

FIG. 4 is a cross-sectional view through line 4—4 of FIG. 3.

DETAILED DESCRIPTION OF PREFERRED EMBODIMENTS

Figure 1:
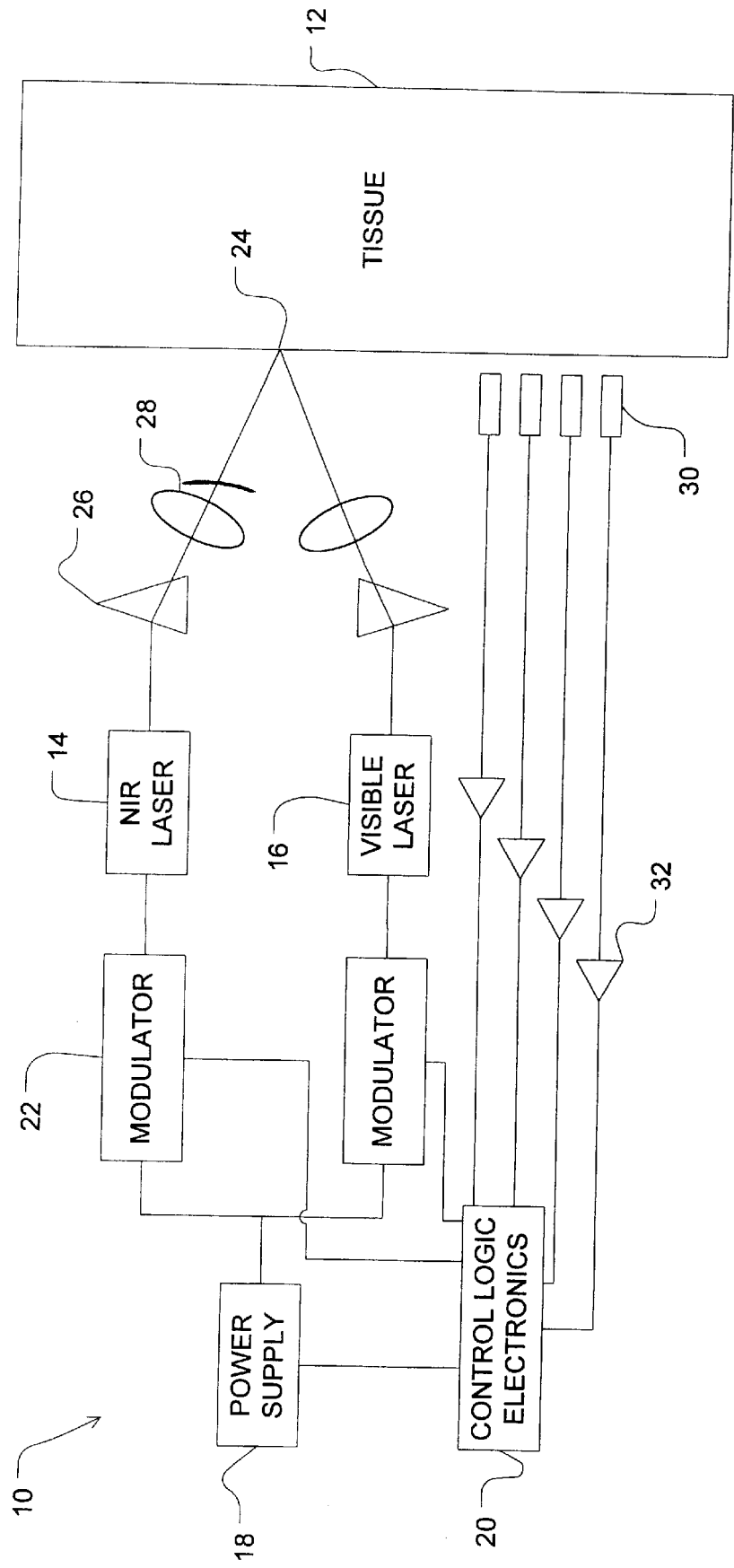
FIG. 1 is a schematic block diagram of an embodiment of the invention.

FIG. 1 shows a general schematic diagram for a preferred laser apparatus 10 of the invention. Laser apparatus 10 is generally useful for treating, e.g., tissue disorders (as used herein, the expression "tissue disorders" denotes disorders associated with the tissues regardless of where such disorders originate or are manifested), such as tissue 12 shown in the figures. Laser apparatus 10 enables a method for treating tissue disorders to at least alleviate certain symptoms of the disorders, such as, e.g., pain.

The laser apparatus 10 of FIG. 1 comprises one near-infrared (NIR) light laser 14 and one visible light laser 16. The lasers 14 and 16 are energized by a power supply 18. The power output from power supply 18 is controlled by control logic electronics 20, either alone or in combination with modulators 22, as shown in the figures. Laser apparatus 10 is thereby adapted to control power density (i.e., irradiance in watts/cm$^2$) delivered to the target tissue 12, as well as the total delivered energy dosage (i.e., radiant exposure in joules/cm$^2$) of radiation.

In embodiments, laser apparatus 10 is adapted to selectively produce pulses of laser light at a frequency of between 0 to 50,000 and preferably 0 to 30,000 pulses per minute, each pulse preferably having a peak intensity of between 0 and 2000 watts/cm$^2$.

NIR laser 14 is adapted to selectively produce laser light having a near-infrared wavelength and the frequency and intensity discussed above. Preferably, NIR laser 14 emits a beam having a wavelength of about 750 to about 1000 nm, more preferably about 900 to about 930 nm, most preferably about 905 nm.

Visible light laser 16 is adapted to selectively produce laser light having a wavelength in the visible light range and the frequency and intensity discussed above. Preferably, visible light laser 16 emits a beam having a wavelength of about 450 to about 749 nm, more preferably about 620 to about 670 nm, most preferably about 660 nm. Lasers 14 and 16 can be the same or different types of laser, and in certain embodiments, lasers 14 and 16 can be merged into a single laser adapted to selectively produce coherent energy at wavelengths within the visible and near-infrared regions of the electromagnetic spectrum. Suitable lasers 14 and 16 according to the invention, include, e.g., noble gas lasers (e.g., argon lasers, helium-neon lasers, etc.), diode lasers and tunable dye lasers.

Each of the beams emitted from lasers 14 and 16 is preferably directed at a common focal point 24 on tissue 12, using a waveguide, such as a converging prism 26 and focusing lens 28, as shown in FIG. 1. Other suitable waveguides include, e.g., lenses having different configurations, a hollow metallic waveguide, a hollow dielectric waveguide, and/or an optical fiber (as discussed below and shown in FIG. 3). Suitable waveguides are also suggested in U.S. Pat. No. 4,963,143 to Pinnow.

In embodiments, the laser beams converge prior to focal point 24, to yield coaxial beams comprising coherent radiation at a visible wavelength and coherent radiation at a near-infrared wavelength. The coaxial beams are preferable to other beam conformations, as the beams penetrate to subsurface regions directly below focal point 24, rather than subsurface regions that are not centered below focal point 24.

In embodiments wherein both beams are emitted by the same laser, the near-infrared beam and the visible beam can be alternately pulsed at focal point 24 to produce a desired effect.

Although dual wavelength laser irradiation is a preferred embodiment of the invention, irradiation with a single wavelength or with more than two wavelengths of coherent radiation also forms a part of this invention, preferably in conjunction with the automated control system described immediately below.

In preferred embodiments, the invention includes an automated control system, comprising feedback-controlled irradiation of target tissues. A preferred laser apparatus according to the invention non-invasively detects, in real-time, the radiant exposure and/or irradiance of radiated energy within the tissue beneath the laser focal point on the surface of the target tissue. In particular, the diffuse reflectance of the visible and/or near-infrared light is detected, thus enabling the determination of the irradiance at a pre-determined depth, and in conjunction with the exposure time, the actual radiant exposure at the predetermined depth.

Thus, detectors 30 are used to monitor the energy characteristics of tissue 12. Preferably, detectors 30 are positioned along a radius originating at focal point 24 to detect the diffuse radiation emitted from tissue 12. At least two detectors 30 are positioned at different points along the radius, and preferably four detectors 30 are so positioned, as shown in the figures. In embodiments, a single detector can be moved along a radius to measure the radial dependence of the diffuse radiation emitted from tissue 12. Detectors 30 suitable for use in the invention include, e.g., optical fibers terminating into fast silicon detectors, gallium arsenide detectors and indium phosphide detectors.

The signals from detectors 30 are preferably amplified by amplifiers 32 before being reported to control logic electronics 20.

Figure 2:
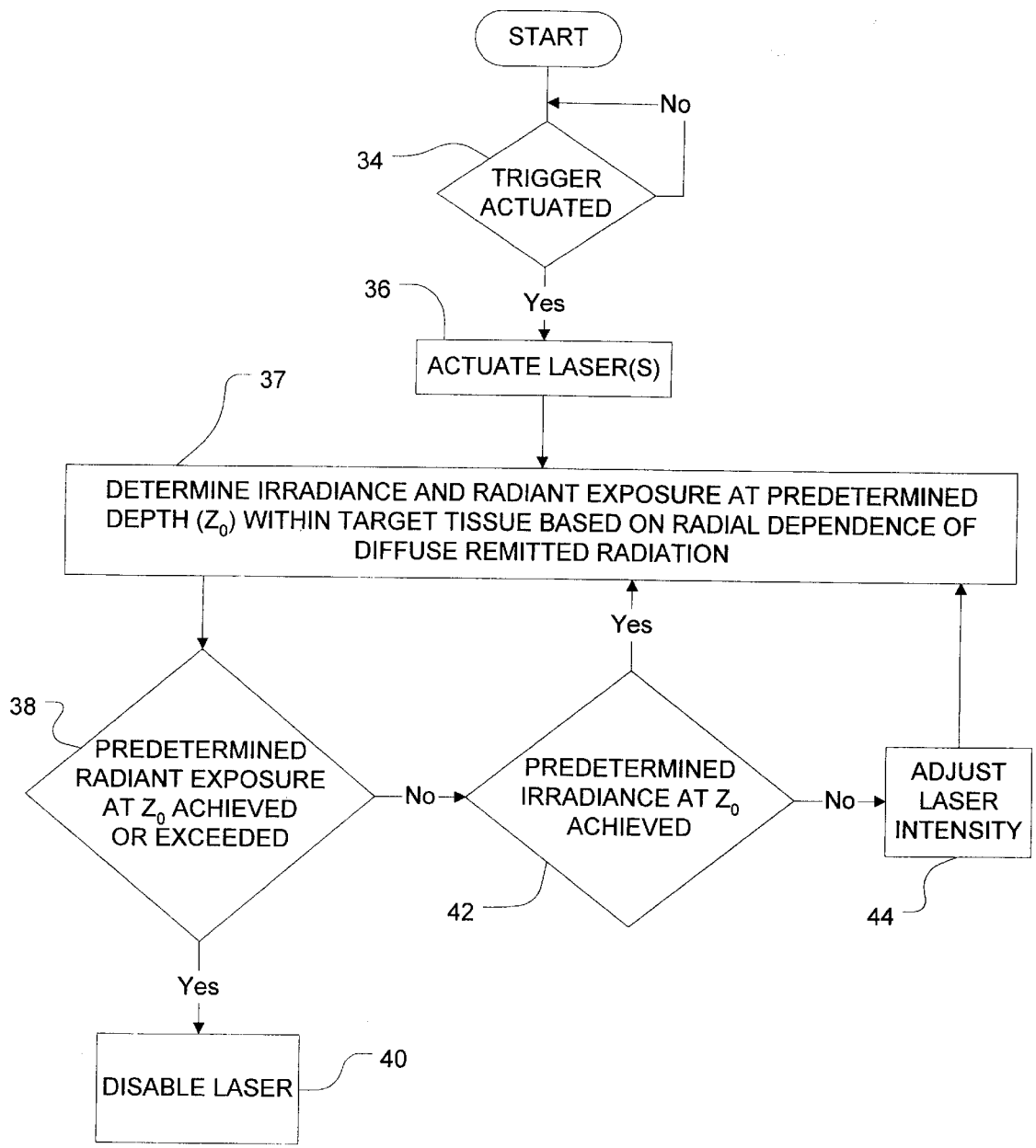
FIG. 2 is a flow diagram of a process executed by the control logic electronics of the embodiment of FIG. 1.

Control logic electronics 20 include a processor (not shown), which executes modules 34–44 (FIG. 2). The processor in control logic electronics 20 detect (in module 34) when user activates a trigger, switch or button (not shown) of laser apparatus 10. When the trigger is depressed, the processor executes module 36 and then module 37. Until the trigger is depressed, the processor continues to execute module 34.

In module 36, control logic electronics 20 actuate lasers 14 and 16, and in module 37, control logic electronics 20 determine the intensity of the radiation at a predetermined depth, $Z_0$, within tissue 12 below focal point 24, and thus the radiant exposure and irradiance at $Z_0$, with known exposure time. This determination is preferably made using an analysis of the radial dependence of diffuse remitted radiation detected by detectors 30 positioned along a radius originating at focal point 24.

The attenuation of the optical radiation from tissue 12 as a function of depth Z is related to the absorption and scattering properties of the tissue, resulting in large variations in the depth distribution of the power/energy. Using a theoretical model of light propagation in turbid media (e.g., tissue 12), such as Diffusion Theory, it can be shown that the radial dependence of the diffuse remitted radiation is also a function of the same optical properties. See, e.g., Farrell et al., "A diffusion theory model of spatially resolved, steady-state diffuse reflectance for the non-invasive determination of tissue optical properties in vivo," 19(4) Med. Phys. 879–88 (1992), and Weersink et al., "Accuracy of non-invasive in vivo measurements of photosensitizer uptake based a on a diffusion model of reflectance spectroscopy," 66(3) Photochem. Photobiol. 326–35 (1997). Hence, the radial dependence of the diffuse reflected radiation contains information regarding subsurface radiation.

Control logic electronics 20 determine the radial dependence of the diffuse reflected radiation from the intensity of the signal relayed to it from each detector 30, and the radial distance of each detector 30 from focal point 24. The radial dependence is then used to estimate the depth dependence of intensity (i.e., the attenuation of intensity as a function of depth) in the tissue being treated. For example, the radial dependence can be used to generate a curve or formula for a curve, which can in turn be used to select a depth dependence curve or formula from a look-up table. In any event, the intensity (or irradiance) of radiation at target depth $Z_0$ is determined from the depth dependence curve or formula, and the radiant exposure at target depth $Z_0$ is determined by, e.g., integration.

After executing module 37, the processor then executes module 38. In module 38, the processor compares the value of the radiant exposure at $Z_0$ to a predetermined radiant exposure value. If the detected radiant exposure is greater than or equal to the predetermined radiant exposure value (which is preferably a therapeutically optimum value), module 40 is executed and lasers 14 and 16 are disabled. Lasers 14 and 16 can be disabled in a variety of ways, including interrupting the supply of power to them from power supply 18, modulating the power supply through modulators 22 to the lasers, and/or modulating the beam exiting lasers 14 and 16 using downstream laser modulators, such as shutters (not shown).

If the detected radiant exposure at $Z_0$ is less than the predetermined radiant exposure, module 42 is executed. In module 42, the processor compares the value of the irradiance at $Z_0$ with a predetermined irradiance (which is preferably a therapeutically optimum value). If the detected irradiance at $Z_0$ is equal to the predetermined irradiance, module 37 is executed again. If the detected irradiance is not equal to the predetermined irradiance, module 44 is executed. Module 44 adjusts the intensity of the appropriate laser(s) in accordance with the discrepancy between the detected irradiance and the predetermined irradiance, and then executes module 37 again.

Control logic electronics 20 are preferably adapted to irradiate tissue 12 with radiation having a preselected peak intensity, average intensity and duration. Preferably, control logic electronics 20 are further provided with sufficient computer memory to store a series of treatment protocols for different ailments and/or patients, eliminating the need to re-program the device after each treatment.

Modulators 22 are included to provide the capability of modulating the output from lasers 14 and 16. Modulation is preferably used for two purposes. First, modulation of laser output is used to control the radiant exposure and irradiance in tissue 12. Second, NIR laser 14 is preferably modulated at a different frequency than visible light laser 16 to enable frequency-filtered detection (e.g., using Fourier transform analysis). The remitted intensity of radiation having a first wavelength modulated by a first carrier frequency, can be distinguished from the remitted intensity of radiation having a second wavelength modulated by a second carrier frequency, by performing lock-in detection at the two different carry frequencies. The attenuation of the two respective wavelengths in the tissue of choice can be quantified by measuring the demodulation of the AC signal and the phase shift compared to the source. The intensity of the radiation emitted from tissue 12 can thus be determined at each of the two frequencies using common detectors.

Of course, other signal filtration systems are also suitable for use in the invention, including, e.g., optical filters and time-resolved filtration systems. Alternatively, a variety of narrow wavelength-specific detectors can be used in the apparatus of the invention to independently detect reflectance of a plurality of wavelengths.

Modulators 20 can be positioned before and/or after lasers 14 and 16. Suitable modulators 20 according to the invention include, e.g., frequency controlled driver circuits or acousto-optic modulators. Modulators 20 need not all be of the same type. For example, the modulators positioned before the lasers can be electrical devices adapted to control the amplitude and/or pulse timing of the laser beams emitted by the lasers, while the modulators after the lasers can be mechanical and/or optical shutters.

FIG. 3 shows an alternative embodiment of the invention, wherein focusing lenses 28 and optical fibers 46 act as waveguides directing the near-infrared laser beam and the visible laser beam through an applicator 48 and into tissue 12. This embodiment of the laser apparatus of the invention is particularly well-suited to treating tissue located in confined areas of the body, such as inside a body cavity, such as the mouth. Applicator 48 is applied to (or brought into close proximity with) tissue 12. Detectors 30 are preferably housed in applicator 48 for ease and precision of use.

In embodiments, applicator 48 is specifically adapted for its intended use. Interchangeable applicators 48 can be provided to customize the functionality of a universally adaptable (or at least widely adaptable) apparatus 10. Thus, for example, applicator 48 can be relatively small for conducting treatment within confined spaces, such as the mouth and endoscopic surgical fields. Applicator 48 can include "floating" detectors 30 and/or "floating" waveguide ends, which maintain close contact between applicator 48 and tissue 12 despite surface irregularities of the tissue or tissue contours (in a manner similar to the spring-loaded laser heads disclosed in U.S. Pat. No. 5,150,704 to Tatebayashi et al.).

FIG. 4 is a cross-sectional view through line 4—4 of FIG. 3, which demonstrates an example of the radial positioning of detectors 30 preferably used to determine the radial dependence of the diffuse reflected light.

In addition to targeting treatment to a single depth, the invention encompasses targeting treatment to a plurality of different depths within a tissue. The multiple depth treatments of the invention can be administered simultaneously, sequentially and/or alternately. For example, a system of the invention can be adapted to target a first depth, reset to target a second depth, reset again to target a third depth, and so forth. In conjunction with the ability of systems of the invention to adjust irradiance, radiant exposure, and wavelength, the ability to target multiple depths provides systems of the invention with superior adaptability to a variety of disorders of a variety of tissues in a variety of patients.

The invention is additionally suitable for monitoring and controlling thermal laser applications, using feedback from the tissue to control laser dosage.

The invention will be illustrated in more detail with reference to the following Example, but it should be understood that the present invention is not deemed to be limited thereto.

EXAMPLE

A forearm of a patient complaining of pain and stiffness associated with carpel tunnel syndrome is treated with laser beams having wavelengths of 660 nm and 905 nm simultaneously. A laser treatment apparatus of the invention is used to automatically monitor and control the application of the laser light to apply the irradiance and radiant exposure so that a predetermined fluence-rate and fluence are achieved at depth Z. The apparatus is actuated and the diffuse reflectance of the laser light is detected at several points along a radius originating at the focal point of the laser light on the tissue surface.

To correlate the reflectance as a function of radius $R(\rho)$ with the fluence-rate as a function of depth $\phi(Z)$, a look-up table is generated using diffusion theory (see Farrell et al., supra). For the look-up table, the reflectance, R, at the position of the detectors ($\rho_{x1} \rightarrow \rho_{xn}$) and the fluence-rate at depth ($Z_1 \rightarrow Z_n$) are calculated for the full range of optical absorption and scattering at 660 nm and 905 nm wavelengths, as reported in the literature for human skin.

In the look-up table, the shape of the reflectance vs. radius (R vs. $\rho_x$) curve is used to select the corresponding fluence-rate vs. depth ($\phi$ vs. Z) curve. The fluence-rate at depth Z (the parameter of interest) is then obtained through interpolation of the data of $\phi$ vs. Z.

The irradiance delivered by the apparatus is adjusted to achieve the predetermined $\phi(Z)$. The adjustment can be limited by reference to predetermined safety limits, such as those published in IEC 825-1, at Table 8 (MPE for skin at 905 nm is about 500 mW and at 660 nm it is about 200 mW).

While the invention has been described in detail and with reference to specific examples thereof, it will be apparent to one skilled in the art that various changes and modifications can be made therein without departing from the spirit and scope thereof.

What is claimed is:

1. A method for treating a patient having a disorder, said method comprising:
    irradiating a tissue of said patient with a near-infrared laser light having a first therapeutically effective intensity and with a visible laser light having a second therapeutically effective intensity;
    automatically monitoring said irradiated tissue to noninvasively determine subsurface intensity of at least one of said near-infrared laser light and said visible laser light, said automatically monitoring comprising analyzing a radial dependence of a diffuse reflectance from said tissue of at least one of said near-infrared laser light and said visible laser light; and
    automatically terminating said irradiating when said monitoring indicates that said near-infrared laser light and said visible laser light have been applied to said tissue in amounts therapeutically effective to treat said disorder.

2. The method of claim 1, wherein said diffuse reflectance is detected from at least two detection points on a surface of said tissue, and wherein said two detection points are at separate positions along a radius originating at a surface focal point of said laser lights.

3. The method of claim 1, further comprising automatically adjusting an intensity of at least one of said near-infrared laser light and said visible laser light in response to information obtained by said monitoring.

4. The method of claim 1, wherein said treating alleviates pain associated with said disorder.

5. The method of claim 1, wherein said treating speeds healing of injuries associated with said disorder.

6. The method of claim 1, wherein said tissue comprises a musculo-skeletal soft-tissue of said patient.

7. The method of claim 1, wherein said tissue comprises skin of said patient.

8. The method of claim 1, wherein said near-infrared laser light has a wavelength of 750 to 1000 nm.

9. The method of claim 1, wherein said visible laser light has a wavelength of 450 to 749 nm.

10. The method of claim 9, wherein said near-infrared laser light has a wavelength of 750 to 1000 nm.

11. The method of claim 1, wherein said near-infrared laser light has a peak intensity of 0 to 2000 watts/cm$^2$.

12. The method of claim 1, wherein said visible laser light has a peak intensity of 0 to 2000 watts/cm$^2$.

13. The method of claim 12, wherein said near-infrared laser light has a peak intensity of 0 to 2000 watts/cm$^2$.

14. The method of claim 13, wherein said near-infrared laser light has a wavelength of 750 to 1000 nm and said visible laser light has a wavelength of 450 to 749 nm.

15. The method of claim 1, wherein said near-infrared laser light and said visible laser light are pulsed.

16. The method of claim 1, wherein said near-infrared laser light is pulsed at a first frequency and said visible laser light is pulsed at a second frequency different from said first frequency, and wherein signals of said near-infrared laser light and said visible laser light are detected by a common sensor and filtered by frequency.

17. The method of claim 1, wherein said irradiating is terminated when said monitoring indicates that at least one of said near-infrared laser light and said visible laser light has penetrated to a sub-surface region of said tissue in an amount therapeutically effective to treat said disorder.

18. A laser apparatus adapted to perform the method of claim 1, said laser apparatus comprising:
    a near-infrared light laser;

a visible light laser;

a power supply in electrical communication with said lasers;

waveguides for guiding beams from said lasers to a common focal point on a surface of a target tissue;

detectors adapted to detect radiation remitted from said target surface along a radius originating at said common focal point; and control logic electronics adapted to automatically adjust an output of said lasers based on said remitted radiation detected by said detectors.

19. A method for administering a predetermined dose of radiation to a distal target tissue, said method comprising:

irradiating a proximal tissue adjacent said distal target tissue with at least one laser light which penetrates through said proximal tissue to administer radiation to said distal target tissue;

automatically monitoring said proximal tissue to determine whether to terminate said irradiating, said monitoring comprising detecting a radial dependence of a diffuse reflectance from a surface of said proximal tissue of said at least one laser light; and automatically terminating said irradiating when said monitoring indicates that said predetermined dose of laser light has been applied to said distal target tissue.

20. The method of claim 19, wherein said diffuse reflectance is detected from at least two detection points on said surface of said proximal tissue, and wherein said two detection points are at separate positions along a radius originating at a surface focal point of said at least one laser light.

21. The method of claim 19, further comprising automatically adjusting an intensity of said at least one laser light.

22. The method of claim 19, wherein said predetermined dose is an amount therapeutically effective to treat a disorder.

23. A laser apparatus adapted to perform the method of claim 19, said laser apparatus comprising:

at least one laser;

a power supply in electrical communication with said at least one laser;

at least one detector adapted to detect radiation remitted from two points on a target surface along a radius originating at a focal point of said at least one laser on said proximal tissue; and control logic electronics adapted to automatically adjust an output of said at least one laser based on said remitted radiation detected by said at least one detector.

* * * * *